(12) United States Patent
Wagner

(10) Patent No.: US 8,221,729 B2
(45) Date of Patent: Jul. 17, 2012

(54) USE OF AMINOPHENYLBENZOTRIAZOLE DERIVATIVES FOR PROTECTING HUMAN AND ANIMAL SKIN AND HAIR FROM THE HARMFUL EFFECTS OF UV RADIATION AND COSMETIC COMPOSITIONS THEREOF

(75) Inventor: Barbara Wagner, Lörrach (DE)

(73) Assignee: BASF SE, Ludwigshafen (DE)

( * ) Notice: Subject to any disclaimer, the term of this patent is extended or adjusted under 35 U.S.C. 154(b) by 670 days.

(21) Appl. No.: 12/309,380

(22) PCT Filed: Jul. 24, 2007

(86) PCT No.: PCT/EP2007/057614
§ 371 (c)(1),
(2), (4) Date: Jan. 15, 2009

(87) PCT Pub. No.: WO2008/012304
PCT Pub. Date: Jan. 31, 2008

(65) Prior Publication Data
US 2009/0246154 A1 Oct. 1, 2009

(30) Foreign Application Priority Data
Jul. 27, 2006 (EP) .................................... 06117959

(51) Int. Cl.
*A61K 7/42* (2006.01)
*A61K 31/41* (2006.01)
*G03C 1/815* (2006.01)

(52) U.S. Cl. .......... 424/59; 430/512; 430/507; 430/523; 430/150; 514/383

(58) Field of Classification Search .................... 424/59; 430/512, 507, 523, 150
See application file for complete search history.

(56) References Cited

U.S. PATENT DOCUMENTS

| | | | | | |
|---|---|---|---|---|---|
| 2,334,348 | A | * | 11/1943 | Miglarese | 424/59 |
| 4,540,648 | A | * | 9/1985 | Scheler | 430/172 |
| 5,667,765 | A | * | 9/1997 | Hansenne et al. | 424/59 |
| 5,739,348 | A | | 4/1998 | Vishwakarma et al. | 548/260 |
| 6,201,000 | B1 | | 3/2001 | Luther et al. | 514/383 |

FOREIGN PATENT DOCUMENTS

| | | |
|---|---|---|
| FR | 1324898 | 4/1963 |
| FR | 2194442 | 3/1974 |
| GB | 2288613 | 10/1995 |
| JP | 50045615 | 4/1975 |
| JP | 11158163 | 6/1999 |

OTHER PUBLICATIONS

English language abstract for JP 11158163, Jun. 15, 1999.
V. L. Mylroie et al., "Novel Synthesis of 2-(2'-Hydroxyphenyl)Benzotriazole Compounds", Catalysis of Organic Reactions, vol. 75, (1998), pp. 479-493.

* cited by examiner

Primary Examiner — Mina Haghighatian
(74) Attorney, Agent, or Firm — Shiela A. Loggins

(57) ABSTRACT

Disclosed are-(2'-Hydroxy-4'-aminophenyl)benzotriazole derivatives of formula

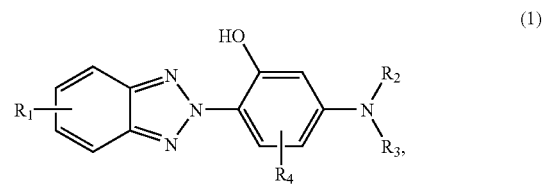

(1)

wherein $R_1$ and $R_4$ independently of each other are hydrogen; $C_1$-$C_{28}$alkyl; $C_1$-$C_{28}$alkoxy; $C_2$-$C_{28}$alkenyl; $C_2$-$C_{28}$alkinyl; $C_3$-$C_{12}$cycloalkyl; $C_3$-$C_{12}$cycloalkenyl; $C_7$-$C_{28}$aralkyl; $C_1$-$C_{20}$heteroalkyl; $C_3$-$C_{12}$cycloheteroalkyl; or $C_5$-$C_{16}$ heteroaralkyl; and wherein $C_1$-$C_{28}$alkyl, $C_1$-$C_{28}$alkoxy, $C_2$-$C_{28}$alkenyl and $C_2$-$C_{28}$alkinyl are unsubstituted or may be substituted by at least one $C_1$-$C_5$alkyl, $C_1$-$C_5$alkoxy or hydroxy;

$R_2$ and $R_3$ independently of each other are hydrogen; $C_1$-$C_{28}$alkyl; $C_2$-$C_{28}$ alkenyl; $C_2$-$C_{22}$alkinyl; $C_3$-$C_{12}$cycloalkyl; $C_3$-$C_{12}$cycloalkenyl; $C_7$-$C_{28}$ aralkyl; $C_1$-$C_{20}$ heteroalkyl; $C_3$-$C_{12}$cycloheteroalkyl; $C_5$-$C_{16}$heteroaralkyl; and wherein $C_1$-$C_{28}$alkyl, $C_1$-$C_{28}$alkoxy, $C_2$-$C_{28}$alkenyl and $C_2$-$C_{28}$alkinyl are unsubstituted or may be substituted by at least one $C_1$-$C_5$alkyl, $C_1$-$C_5$alkoxy or hydroxy; or CO—$R_5$; or $R_2$ and $R_3$ together with the linking nitrogen form a 5- to 7-membered, monocyclic, carbocyclic or heterocyclic ring;

$R_5$ is $C_1$-$C_{28}$alkyl; $C_2$-$C_{28}$alkenyl; $C_2$-$C_{28}$alkinyl; $C_3$-$C_{12}$cycloalkyl; $C_3$-$C_{12}$cycloalkenyl; $C_7$-$C_{20}$aralkyl; $C_1$-$C_{20}$ heteroalkyl; $C_3$-$C_{12}$ cycloheteroalkyl; $C_1$-$C_5$alkoxycarbonyl-$C_1$-$C_5$alkyl; or $C_5$-$C_{16}$heteroaralkyl;

for protecting human and animal hair and skin from harmful effects of UV radiation.

17 Claims, No Drawings

USE OF AMINOPHENYLBENZOTRIAZOLE DERIVATIVES FOR PROTECTING HUMAN AND ANIMAL SKIN AND HAIR FROM THE HARMFUL EFFECTS OF UV RADIATION AND COSMETIC COMPOSITIONS THEREOF

The present invention relates to the use of specific benzotriazole UV absorbers for protecting human and animal hair and skin from the harmful effects of UV radiation and cosmetic compositions comprising these compounds.

Therefore, the present invention relates to the use of 2-(2'-Hydroxy-4'-aminophenyl)benzotriazole derivatives of formula

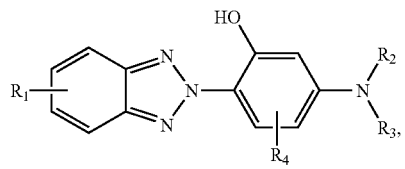

(1)

wherein
$R_1$ and $R_4$ independently of each other are hydrogen; $C_1$-$C_{28}$alkyl; $C_1$-$C_{28}$alkoxy; $C_2$-$C_{28}$alkenyl; $C_2$-$C_{28}$alkinyl; $C_3$-$C_{12}$cycloalkyl; $C_3$-$C_{12}$cycloalkenyl; $C_7$-$C_{28}$aralkyl; $C_1$-$C_{20}$heteroalkyl; $C_3$-$C_{12}$cycloheteroalkyl; or $C_5$-$C_{16}$ heteroaralkyl; and wherein $C_1$-$C_{28}$alkyl, $C_1$-$C_{28}$alkoxy, $C_2$-$C_{28}$alkenyl and $C_2$-$C_{28}$alkinyl are unsubstituted or may be substituted by at least one $C_1$-$C_5$alkyl, $C_1$-$C_5$alkoxy or hydroxy;
$R_2$ and $R_3$ independently of each other are hydrogen; $C_1$-$C_{28}$alkyl; $C_2$-$C_{28}$ alkenyl; $C_2$-$C_{22}$alkinyl; $C_3$-$C_{12}$cycloalkyl; $C_3$-$C_{12}$cycloalkenyl; $C_7$-$C_{28}$ aralkyl; $C_1$-$C_{20}$ heteroalkyl; $C_3$-$C_{12}$cycloheteroalkyl; $C_5$-$C_{16}$heteroaralkyl; and wherein $C_1$-$C_{28}$alkyl, $C_1$-$C_{28}$alkoxy, $C_2$-$C_{28}$alkenyl and $C_2$-$C_{28}$alkinyl are unsubstituted or may be substituted by at least one $C_1$-$C_5$alkyl, $C_1$-$C_5$alkoxy or hydroxy; or CO—$R_5$; or
$R_2$ and $R_3$ together with the linking nitrogen form a 5- to 7-membered, monocyclic, carbocyclic or heterocyclic ring;
$R_5$ is $C_1$-$C_{28}$alkyl; $C_2$-$C_{28}$alkenyl; $C_2$-$C_{28}$alkinyl; $C_3$-$C_{12}$cycloalkyl; $C_3$-$C_{12}$cycloalkenyl; $C_7$-$C_{20}$aralkyl; $C_1$-$C_{20}$ heteroalkyl; $C_3$-$C_{12}$ cycloheteroalkyl; $C_1$-$C_5$alkoxycarbonyl-$C_1$-$C_5$alkyl; or $C_5$-$C_{16}$heteroaralkyl; and
n is 1, 2, 3 or 4;
for protecting human and animal hair and skin from harmful effects of UV radiation.

Alkyl, cycloalkyl, alkenyl or cycloalkenyl radicals can be straight-chain or branched or also monocyclic or polycyclic.

Alkyl can be for example straight-chain $C_1$-$C_{28}$ alkyl or preferably branched $C_3$-$C_{12}$ alkyl, for example methyl, ethyl, n-propyl, isopropyl, n-butyl, sec.-butyl, isobutyl, tert.-butyl, n-pentyl, 2-pentyl, 3-pentyl, 2,2-dimethylpropyl, n-hexyl, n-octyl, 1,1,3,3-tetramethylbutyl, 2-ethylhexyl, nonyl, decyl, n-octadecyl, eicosyl, or dodecyl.

$C_3$-$C_{12}$cycloalkyl is for example cyclopropyl, cyclobutyl, cyclopentyl, cyclohexyl, trimethylcyclohexyl, menthyl, thujyl, bornyl, 1-adamantyl or 2-adamantyl.

Alkenyl can be e.g. straight-chain $C_2$-$C_{28}$ alkenyl or preferably branched $C_3$-$C_{12}$ alkenyl.

$C_2$-$C_{28}$alkenyl or $C_3$-$C_{12}$cycloalkenyl refers to unsaturated hydrocarbon residues containing one or multiple double bonds such vinyl, allyl, 2-propen-2-yl, 2-buten-1-yl, 3-buten-1-yl, 1,3-butadien-2-yl, 2-cyclobuten-1-yl, 2-penten-1-yl, 3-penten-2-yl, 2-methyl-1-buten-3-yl, 2-methyl-3-buten-2-yl, 3-methyl-2-buten-1-yl, 1,4-pentadien-3-yl, 2-cyclopenten-1-yl, 2-cyclohexen-1-yl, 3-cyclohexen-1-yl, 2,4-cyclohexadien-1-yl, 1-p-menthen-8-yl, 4(10)-thujen-10-yl, 2-norbornen-1-yl, 2,5-norbornadien-1-yl, 7,7-dimethyl-2,4-norcaradien-3-yl or signifies different isomers of hexenyl, octenyl, nonenyl, decenyl or dodecenyl.

$C_7$-$C_{28}$ aralkyl is for example benzyl, 2-benzyl-2-propyl, β-phenyl-ethyl, 9-fluorenyl, α,α-dimethylbenzyl, ω-phenyl-butyl, ω-phenyl-octyl, ω-phenyl-dodecyl oder 3-methyl-5-(1',1',3',3'-tetramethyl-butyl)-benzyl.

$C_7$-$C_{28}$ aralkyl can be unsubstituted or substituted at the alkyl- as well at the aryl-moiety of the aralkyl-group, but is preferably substituted at the aryl-moiety.

$C_5$-$C_{16}$heteroaralkyl is for example a $C_1$-$C_8$ alkyl moiety which is substituted with a $C_4$-$C_8$heteroaryl group.

Preferably in formula (I)
$R_1$ is hydrogen; $C_1$-$C_{28}$alkyl; or $C_1$-$C_{28}$alkoxy, more preferably hydrogen; $C_1$-$C_5$alkyl; or $C_1$-$C_5$alkoxy; most preferably hydrogen; methyl, tert. butyl; or methoxy;
Preferably in formula (1)
$R_4$ is hydrogen; or $C_1$-$C_5$alkyl; more preferably hydrogen.
Preferably in formula (1),
$R_2$ is hydrogen; $C_1$-$C_{28}$alkyl; $C_2$-$C_{28}$ alkenyl; and wherein $C_1$-$C_{28}$alkyl and $C_2$-$C_{28}$alkenyl are unsubstituted or may be substituted by at least one $C_1$-$C_5$alkyl, $C_1$-$C_5$alkoxy or hydroxy; or CO—$R_5$; and
$R_5$ is $C_1$-$C_{28}$alkyl; $C_1$-$C_5$alkoxycarbonyl-$C_1$-$C_5$alkyl; or $C_3$-$C_{12}$cycloalkyl.
Preferably,
$R_2$ is hydrogen; $C_1$-$C_{10}$alkyl; $C_2$-$C_{10}$ alkenyl; and wherein $C_2$-$C_{10}$alkenyl is unsubstituted or may be substituted by $C_1$-$C_5$alkoxy; CO—$R_5$;
$R_5$ is $C_1$-$C_{10}$alkyl; $C_1$-$C_5$alkoxycarbonyl-$C_1$-$C_5$alkyl; or $C_3$-$C_{12}$cycloalkyl.
More preferably,
$R_2$ is hydrogen; $C_1$-$C_5$alkyl; *-$C_1$-$C_4$alkylene-HC=CH—O—$C_1$-$C_5$alkyl; or CO—$R_5$; and
$R_5$ is $C_1$-$C_{10}$alkyl; —$CH_2$—$CH_2$(CO)—O—$C_2H_5$; or cyclohexyl; most preferably $R_5$ is isooctyl.
Preferably in formula (1),
$R_3$ is hydrogen; or *-(CO)—$CH_3$.
Preferred are also compounds of formula (1), wherein $R_2$ and $R_3$ have the same meaning; more preferably, wherein $R_2$ and $R_3$ are $C_1$-$C_5$alkyl.
Preferred are also compounds of formula (1), wherein $R_2$ and $R_3$ together with the linking nitrogen form the heterocyclic ring radical of formula

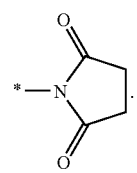

(1a)

Preferred compounds of formula (I) are those, wherein
$R_1$ is hydrogen; $C_1$-$C_5$alkyl; or $C_1$-$C_5$alkoxy;
$R_4$ is hydrogen; or $C_1$-$C_5$alkyl;
$R_2$ is hydrogen; $C_1$-$C_{10}$alkyl; $C_2$-$C_{10}$ alkenyl; and wherein $C_2$-$C_{10}$alkenyl is unsubstituted or may be substituted by $C_1$-$C_5$alkoxy; or CO—$R_5$;

$R_5$ is $C_1$-$C_{10}$alkyl; $C_1$-$C_5$alkoxycarbonyl-$C_1$-$C_5$alkyl; or $C_3$-$C_{12}$cycloalkyl;
$R_3$ is hydrogen; or *-(CO)—CH$_3$; and more preferably those, wherein
$R_1$ is hydrogen; or $C_1$-$C_5$alkyl;
$R_2$ is CO—$R_5$;
$R_3$ is hydrogen;
$R_5$ is isooctyl; and
$R_4$ is hydrogen.

Examples of preferred aminobenzotriazols of the present invention are listed in Table 1:

TABLE 1

Aminobenzotriazoles of the present invention

BT-01
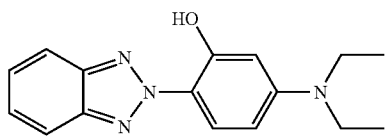

BT-02
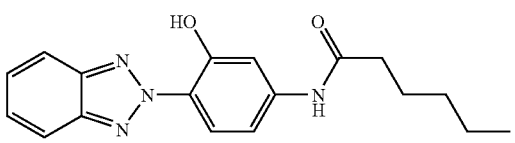

BT-03
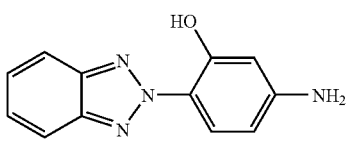

BT-04
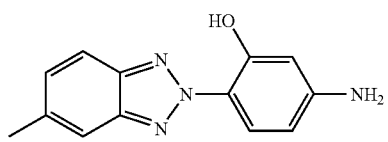

BT-05
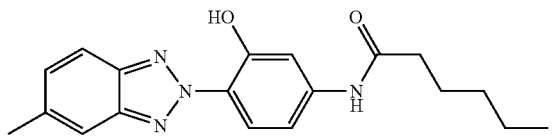

BT-06
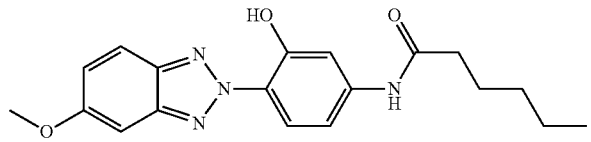

BT-07
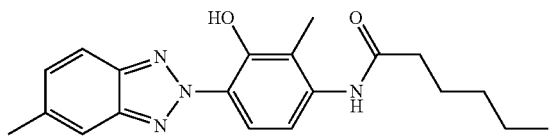

BT-08
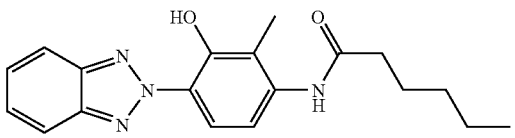

BT-09
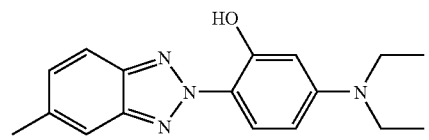

TABLE 1-continued

Aminobenzotriazoles of the present invention

BT-10

BT-11

BT-12

BT-13

BT-14

BT-15

BT-16

BT-17

BT-18

TABLE 1-continued

Aminobenzotriazoles of the present invention

BT-19

BT-20

BT-21

BT-22

BT-23

BT-24

BT-25

BT-26

BT-27

TABLE 1-continued

Aminobenzotriazoles of the present invention

BT-28

BT-29

BT-30

BT-31

BT-32

The benzotriazole derivatives of formula (1) may be prepared starting from a 2-nitroaniline derivative which is then diazotized. The resulting diazonium intermediate reacts with 3-amino- or 3-amino alkyl-substituted phenols to the corresponding azo dye which is reduced to the desired benzotriazole derivative.

X = OH, NH$_2$, NEt$_2$

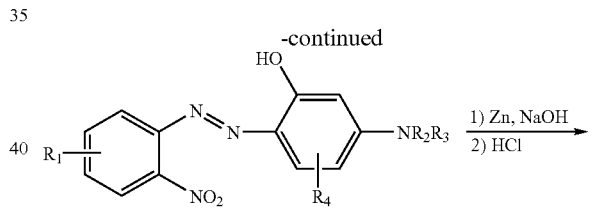

Another method for the preparation of N-alkylated benzotriazole UV absorbers according to the present invention is to alkylate a $R_1$-/$R_4$-substituted 2-(2'-hydroxy-4'-aminophenyl) benzotriazole at the amino group. The alkylation can be achieved by conventional alkylation methods. One method may be to use alkylhalogenides like alkylbromides or alkyl chlorides as alkylating reagent and sodium hydride or another deprotonating reagent. The reaction is then carried out in a suitable solvent like toluene, pyridine or polar aprotic solvents such as e.g. 1-methyl-2-pyrrolidone, dimethylformamide, dimethylsulfoxide, dioxane, tetrahydrofuran, acetonitrile and the like. The alkylation can be carried out once resulting in the corresponding 4'-monoalkylamino benzotriazole derivatives or can be carried out twice resulting in the corresponding 4'-dialkylamino benzotriazole compounds.

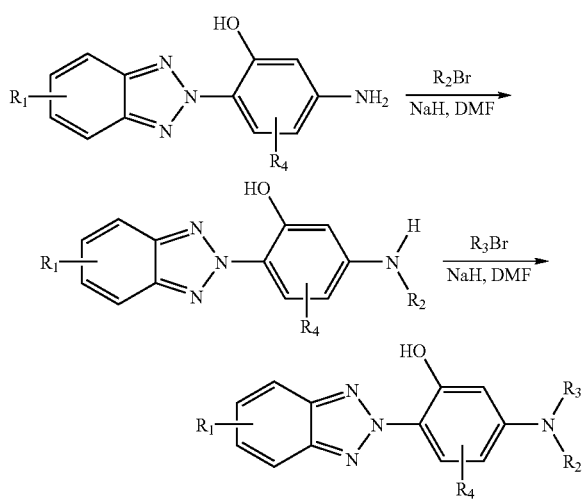

According to the above mentioned method the R$_1$-/R$_4$-substituted 2-(2'-hydroxy-4'-aminophenyl)benzotriazole may also be acylated at the amino group by using known acylating methods. A convenient method is using acyl halides as acylating reagents in a suitable solvent like toluene or pyridine in the presence of an acid acceptor, such as a mild base. In the case pyridine is used as a solvent, it can also serve as an acid acceptor.

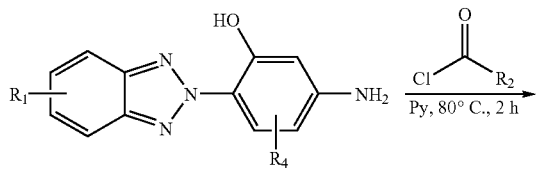

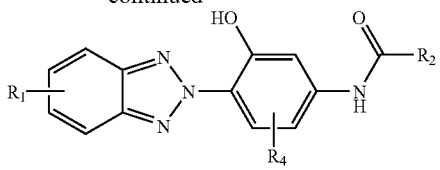

The monoacylated benzotriazoles may subsequently be acylated to the corresponding N,N-diacylated benzotriazole derivatives or may also be alkylated in another step to the corresponding N-alkylated benzotriazolylphenyl amide compounds.

The compounds of formula (1) according to the present invention are particularly suitable as UV filters, i.e. for protecting ultraviolet-sensitive organic materials, in particular the skin and hair of humans and animals, from the harmful effects of UV radiation. These compounds are therefore suitable as sunscreens in cosmetic, pharmaceutical and veterinary medical preparations. These compounds can be used both in dissolved form and in the micronized state.

Furthermore, the compounds of formula (1) are useful as anti-wrinkle perception modifiers.

The UV absorbers according to the present invention are preferably used in the dissolved state (soluble organic filters, solubilized organic filters).

The cosmetic formulations or pharmaceutical compositions according to the present invention may additionally contain one or more than one further UV filter as listed in Table 2.

TABLE 2

Suitable UV filter substances which can be additionally used with the UV absorbers according to the present invention

| | |
|---|---|
| DE 10013318 | T 1 pp 8-9, all Examples pp 10-13, T 2 pp 13-14, all Examples p 14, Ex A, B, C, D, E, F pp 19-20 |
| DE102004038485A1 | Formula 1 on p 2; Ex 1-4 on p 13; |
| DE102004039281A1 | Formulas I-II on p 1; Ex Ia-Iae on pp 7-12; Ex IIa-IIm on pp 14-15; Ex 1-25 on pp 42-56; |
| DE 10206562 A1 | Ex 1-3 p 10, Ex 4-7 p 11, Ex 8-15 pp 12-14 |
| DE 10238144 A1 | Ex on p 3-5; |
| DE 10331804 | T 1 p 4, T 2 + 3 p 5 |
| DE 19704990 A1 | Ex 1-2 on pp 6-7; |
| EP 613 893 | Ex 1-5 + 15, T 1, pp 6-8 |
| EP 0 998 900 A1 | Ex on pp 4-11 |
| EP 1 000 950 | Comp. In Table 1, pp 18-21 |
| EP 1 005 855 | T 3, p 13 |
| EP 1 008 586 | Ex 1-3, pp 13-15 |
| EP 1 008 593 | Ex 1-8, pp 4-5 |
| EP 1 027 883 | Compound VII, p 3 |
| EP 1 027 883 | Comp I-VI, p 3 |
| EP 1 028 120 | Ex 1-5, pp 5-13 |
| EP 1 059 082 | Ex 1; T 1, pp 9-11 |
| EP 1 060 734 | T 1-3, pp 11-14 |
| EP 1 064 922 | Compounds 1-34, pp 6-14 |
| EP 1 077 246 A2 | Ex 1-16 on pp 5-11; |
| EP 1 081 140 | Ex 1-9, pp 11-16 |
| EP 1 103 549 | Compounds 1-76, pp 39-51 |
| EP 1 108 712 | 4,5-Dimorph olino-3-hydroxypyridazine |
| EP 1 123 934 | T 3, p 10 |
| EP 1 129 695 | Ex 1-7, pp 13-14 |
| EP 1 167 359 | Ex 1, p 11 and Ex 2, p 12 |

TABLE 2-continued

Suitable UV filter substances which can be additionally used
with the UV absorbers according to the present invention

| | |
|---|---|
| EP 1 232 148 B1 | Ex 4-17 on pp 3-5; |
| EP 1 258 481 | Ex 1, pp 7, 8 |
| EP 1 310 492 A1 | Ex 1-16 on pp 22-30 |
| EP 1 371 654 A1 | Ex on pp 5-7 |
| EP 1 380 583 A2 | Ex 1, p 6; |
| EP 1 423 351 A2 | Ex 1-16 on pp 31-37; |
| EP 1 423 371 A1 | T 1 on pp 4-8, Ex on p 9, Ex 1-9 on pp 36-42; |
| EP 1 454 896 A1 | Ex 1-5 on pp 10-13, Examples on pp 4-5; |
| EP 1 471 059 A1 | Ex 1-5 on pp 4-5; |
| EP 1484051 A2 | Formula III-VII on pp 18-19, Ex 7-14 on pp 7-9, Ex 18-23 on pp 11-12, Ex 24-40 on pp 14-17; |
| EP 1648849 A2 | Formula 1 on p 4; Ex 1-2 on pp 13-17; Ex C10 and O10 on pp 15-16; |
| EP 420 707 B1 | Ex 3, p 13 (CAS Reg. No 80142-49-0) |
| EP 503 338 | T 1, pp 9-10 |
| EP 517 103 | Ex 3, 4, 9, 10 pp 6-7 |
| EP 517 104 | Ex 1, T 1, pp 4-5; Ex 8, T 2, pp 6-8 |
| EP 626 950 | all compounds |
| EP 669 323 | Ex 1-3, p 5 |
| EP 743 309 A1 | Ex 1-12 on pp 18-24; |
| EP 780 382 | Ex 1-11, pp 5-7 |
| EP 823 418 | Ex 1-4, pp 7-8 |
| EP 826 361 | T 1, pp 5-6 |
| EP 832 641 | Ex 5 + 6 p 7; T 2, p 8 |
| EP 832 642 | Ex 22, T 3, pp 10-15; T 4, p 16 |
| EP 848944 A2 | Formulas I and II on p 1; Ex on p 8; Examples on p 10; |
| EP 852 137 | T 2, pp 41-46 |
| EP 858 318 | T 1, p 6 |
| EP 863 145 | Ex 1-11, pp 12-18 |
| EP 878 469 A1 | T 1, pp 5-7; |
| EP 895 776 | Comp. In rows 48-58, p 3; R 25 + 33, p 5 |
| EP 911 020 | T 2, pp 11-12 |
| EP 916 335 | T 2-4, pp 19-41 |
| EP 924 246 | T 2, p 9 |
| EP 933 376 | Ex 1-15, pp 10-21 |
| EP 944 624 | Ex 1 + 2, pp 13-15 |
| EP 945 125 | T 3 a + b, pp 14-15 |
| EP 95 097 | Ex 1, p 4 |
| EP 967 200 | Ex 2; T 3-5, pp 17-20 |
| EP 969 004 | Ex 5, T 1, pp 6-8 |
| FR 2842806 A1 | Ex I p 10, Ex II p 12 |
| FR 2861075 A1 | Ex 1-3 on pp 12-14; |
| FR 2862641 | Formula 3 on p 4; Ex A-J on pp 7-9; |
| FR 2869907 A1 | Formula 1 on p 6; T 1 on p 7-8; Ex 4-39 on pp 12-35; |
| KR 2004025954 | all kojyl benzoate derivatives |
| JP 06135985 A2 | Formula 1 on p 2; Ex 1-8 on pp 7-8; |
| JP 2000319629 | CAS Reg Nos. 80142-49-0, 137215-83-9, 307947-82-6 |
| JP 2003081910 A | Ex on p 1; |
| JP 2005289916 A | Formula I on p 1 ; Ex Ia-Id on pp 2-3; |
| JP 2005290240 A | Formulas I on p 2, Ex II on p 2; |
| US 2003/0053966A1 | Ex on pp 3-6 |
| US 2004057912 A1 | Ex on p 7-9, Ex 1 on p 10; |
| US 2004057914 A1 | Ex on p 8-12, Ex 1 on p 12; |
| US 2004/0057911A1 | Formula I and II on p 1; formula III and IV on p 3; Ex 1-3 on pp 5-6; |
| US 2004/0071640A1 | Ex 1-12 on pp 4-7; |
| US 2004/0091433A1 | Ex 1-6 on pp 14-16; |
| US 2004/0136931A1 | Ex 1-3 on p 7; |
| US 2004/0258636A1 | Ex 1-11 on pp 9-15; |
| US 2005/0019278A1 | Ex 1-9 on pp 6-8; |
| US 2005/0136012A1 | Formula 1 on p 2; |
| US 2005/0136014A1 | Formula a-c on p 2; Examples on p 3; |
| US 2005/0201957A1 | Formula 1 on p 1; Ex A, B, C, D, E, F, G on pp 2-3; |
| US 2005/0249681A1 | all compounds on pp 2-3, Ex 1 on p 6; |
| US 2005186157A1 | Formula 1 on p 1; Ex 1-6 on pp 2-4; |
| US 2005260144A1 | Formula I on p 1; Formula II on p 3; Ex 1-10 on pp 8-11; |
| US 2006018848A1 | Ex a-p on pp 3-4; |
| US 2006045859A1 | Formula 1 on p 1; Ex 1-10 on pp 2-4; |
| U.S. Pat. No. 5,635,343 | all compounds on pp 5-10 |
| U.S. Pat. No. 5,332,568 | Ex 1, p 5, T 1 + 2, pp 6-8 |
| U.S. Pat. No. 5,338,539 | Ex 1-9, pp 3 + 4 |
| U.S. Pat. No. 5,346,691 | Ex 40, p 7; T 5, p 8 |
| U.S. Pat. No. 5,801,244 | Ex 1-5, pp 6-7 |
| U.S. Pat. No. 6,613,340 | Ex I, II pp 9-11, Examples on rows 28-53 p 6 |
| U.S. Pat. No. 6,800,274 B2 | Formulas I-VI and IX-XII on pp 14-18; |
| U.S. Pat. No. 6,890,520 B2 | Ex 1-10 on pp 6-9; |
| U.S. Pat. No. 6,926,887 B2 | Ex A on pp 5/6; Formulas I - VIII on pp 27-29; |
| U.S. Pat. No. 6,936,735 B2 | Formulas 1-2 on p 2; formula 3-4 on p 6; |

TABLE 2-continued

Suitable UV filter substances which can be additionally used
with the UV absorbers according to the present invention

| | |
|---|---|
| U.S. Pat. No. 6,962,692 B2 | Formulas VII and VIII on p 6; Formulas I, II, IV-VI, IX, X on pp 14-16; Formula III on p 19; |
| WO 0149686 | Ex 1-5, pp 16-21 |
| WO 0168047 | Tables on pp 85-96 |
| WO 0181297 | Ex 1-3, pp 9-11 |
| WO 0191695 | Formula I on p 4, T on p 8 |
| WO 0202501 A1 | Ex Ia-c, p 5 |
| WO 02069926 A1 | Ex on p 9, Ex on pp 17-23 |
| WO 02072583 | T on pp 68-70 |
| WO 02080876 | Ex 1 on pp 7-9 |
| WO 0238537 | All compounds p 3, compounds on rows 1-10 p 4 |
| WO 03004557 A1 | Ex A1-A29 on pp 36-57; |
| WO 03007906 | Ex I-XXIII, pp 42-48 |
| WO 03086341 A2 | Formula 2-21, pp 4-6; |
| WO 03092643 A1 | T on pp 34-35, compounds listed on p 16 |
| WO 03097577 A1 | Ex on pp 6-8; Ex 1-3 on pp 15-18; |
| WO 03104183 A1 | Formula I-IV on p 1; Ex 1-5 on pp 27-28; |
| WO 04000256 A1 | Ex 1-10 on pp 18-24 |
| WO 04020398 A1 | Ex 1-3 on pp 14-17 |
| WO 04020398 A1 | Formulas I-VI on pp 21-24, Formula IX on p 25; |
| WO 04075871 | Ex 1-3 on pp 17-18; Ex 7-9 on pp 21-22; |
| WO 05009938 A2 | Formula I on p 1; Ex 1-2 on pp 14-15; |
| WO 05065154 A2 | Formula a-c on pp 5-6; |
| WO 05080341 A1 | Formula 1 on p 3; Examples on pp 9-13; |
| WO 05107692 A1 | Formula 1 on p 2; Ex 1-9 on pp 27-29; |
| WO 05118562 A1 | Formula I on p 4; Ex Ia-Ig on p 5; |
| WO 05121108 A1 | Formula I on p 3; Formula Ia on p 5; T 1 on p 7; Ex 3-22 on pp 11-23; |
| WO 06009451 | T 1 on pp 5-8; Formulas III and UVO on p 9; |
| WO 06016806 | T 1 on pp 6-7; T 2 on p 10; T 3 on p 11; T 4 on p 15; |
| WO 06032741 | Formulas 1-3 on p 1; Ex a-k on pp 5-7; Ex 1-4 on pp 18-20; |
| WO 9217461 | Ex 1-22, pp 10-20 |
| WO 9220690 | Polymeric Comp in Examples 3-6 |
| WO 9301164 | T 1 + 2, pp 13-22 |
| WO 9714680 | Ex 1-3, p 10 |

(Abbreviations T: Table, R: row, Comp: compound, Ex: compound(s) of Patent Example, p: page; the generic scope of the UV absorbers is described in the left-hand column; specific compounds are indicated in the right-hand column)

The cosmetic or pharmaceutical preparations can be prepared by physically mixing the UV absorber(s) with the adjuvant using customary methods, for example by simply stirring together the individual components, especially by making use of the dissolution properties of already known cosmetic UV absorbers, like octyl methoxy cinnamate, salicylic acid isooctyl ester, etc. The UV absorber can be used, for example, without further treatment, or in the micronised state, or in the form of a powder.

Cosmetic or pharmaceutical preparations contain from 0.05-40% by weight, based on the total weight of the composition, one UV absorber or UV absorber mixtures.

Preference is given to the use of mixing ratios of the UV absorber of formula (1) according to the present invention and optionally further light-protective agents (as described in Table 2) from 1:99 to 99:1, preferably from 1:95 to 95:1 and most preferably from 10:90 to 90:10, based on weight. Of special interest are mixing ratios of from 20:80 to 80:20, preferably from 40:60 to 60:40 and most preferably approximately 50:50. Such mixtures can be used, inter alia, to improve the solubility or to increase UV absorption.

The UV absorbers of formula (1) according to the present invention or combinations of UV filters are useful to protect skin, hair and/or natural or artificial hair color.

The cosmetic or pharmaceutical preparations may be, for example, creams, gels, lotions, alcoholic and aqueous/alcoholic solutions, emulsions, wax/fat compositions, stick preparations, powders or ointments. In addition to the above mentioned UV filters, the cosmetic or pharmaceutical preparations may contain further adjuvants as described below.

As water- and oil-containing emulsions (e.g. W/O, O/W, O/W/Q and W/O/W emulsions or microemulsions) the preparations contain, for example, from 0.1 to 30% by weight, preferably from 0.1 to 15% by weight and especially from 0.5 to 10% by weight, based on the total weight of the composition, of one or more UV absorbers, from 1 to 60% by weight, especially from 5 to 50% by weight and preferably from 10 to 35% by weight, based on the total weight of the composition, of at least one oil component, from 0 to 30% by weight, especially from 1 to 30% by weight and preferably from 4 to 20% by weight, based on the total weight of the composition, of at least one emulsifier, from 10 to 90% by weight, especially from 30 to 90% by weight, based on the total weight of the composition, of water, and from 0 to 88.9% by weight, especially from 1 to 50% by weight, of further cosmetically acceptable adjuvants.

The cosmetic or pharmaceutical compositions/preparations according to the invention may also contain one or one more additional compounds like fatty alcoholsEsters of fatty acids, natural or synthetic triglycerides including glyceryl esters and derivatives, pearlescent waxes, hydrocarbon oils, silicones or siloxanes (organosubstituted polysiloxanes), fluorinated or perfluorinated oils, emulsifiers, super-fatting agents, surfactants, consistency regulators/thickeners and rheology modifiers, polymers, biogenic active ingredients, deodorising active ingredients, anti-dandruff agents, antioxidants, hydrotropic agents, preservatives and bacteria-inhibiting agents, perfume oils, colourants, polymeric beads or hollow spheres as SPF enhancers.

Cosmetic or Pharmaceutical Preparations

Cosmetic or pharmaceutical formulations are contained in a wide variety of cosmetic preparations. There come into consideration, for example, especially the following preparations:

skin-care preparations, e.g. skin-washing and cleansing preparations in the form of tablet-form or liquid soaps, soapless detergents or washing pastes, bath preparations, e.g. liquid (foam baths, milks, shower preparations) or solid bath preparations, e.g. bath cubes and bath salts;

skin-care preparations, e.g. skin emulsions, multi-emulsions or skin oils;

cosmetic personal care preparations, e.g. facial make-up in the form of day creams or powder creams, face powder (loose or pressed), rouge or cream make-up, eye-care preparations, e.g. eyeshadow preparations, mascara, eyeliner, eye creams or eye-fix creams; lip-care preparations, e.g. lipsticks, lip gloss, lip contour pencils, nail-care preparations, such as nail varnish, nail varnish removers, nail hardeners or cuticle removers;

foot-care preparations, e.g. foot baths, foot powders, foot creams or foot balsams, special deodorants and antiperspirants or callus-removing preparations;

light-protective preparations, such as sun milks, lotions, creams or oils, sunblocks or tropicals, pre-tanning preparations or after-sun preparations;

skin-tanning preparations, e.g. self-tanning creams;

depigmenting preparations, e.g. preparations for bleaching the skin or skin-lightening preparations;

insect-repellents, e.g. insect-repellent oils, lotions, sprays or sticks;

deodorants, such as deodorant sprays, pump-action sprays, deodorant gels, sticks or roll-ons;

antiperspirants, e.g. antiperspirant sticks, creams or roll-ons;

preparations for cleansing and caring for blemished skin, e.g. synthetic detergents (solid or liquid), peeling or scrub preparations or peeling masks;

hair-removal preparations in chemical form (depilation), e.g. hair-removing powders, liquid hair-removing preparations, cream- or paste-form hair-removing preparations, hair-removing preparations in gel form or aerosol foams;

shaving preparations, e.g. shaving soap, foaming shaving creams, non-foaming shaving creams, foams and gels, preshave preparations for dry shaving, aftershaves or aftershave lotions;

fragrance preparations, e.g. fragrances (eau de Cologne, eau de toilette, eau de parfum, parfum de toilette, perfume), perfume oils or perfume creams;

cosmetic hair-treatment preparations, e.g. hair-washing preparations in the form of shampoos and conditioners, hair-care preparations, e.g. pretreatment preparations, hair tonics, styling creams, styling gels, pomades, hair rinses, treatment packs, intensive hair treatments, hair-structuring preparations, e.g. hair-waving preparations for permanent waves (hot wave, mild wave, cold wave), hair-straightening preparations, liquid hair-setting preparations, hair foams, hairsprays, bleaching preparations, e.g. hydrogen peroxide solutions, lightening shampoos, bleaching creams, bleaching powders, bleaching pastes or oils, temporary, semi-permanent or permanent hair colourants, preparations containing self-oxidising dyes, or natural hair colourants, such as henna or camomile.

Presentation Forms

The final formulations listed may exist in a wide variety of presentation forms, for example:

in the form of liquid preparations as a W/O, O/W, O/W/O, W/O/W or PIT emulsion and all kinds of microemulsions, in the form of a gel, in the form of an oil, a cream, milk or lotion, in the form of a powder, a lacquer, a tablet or make-up, in the form of a stick, in the form of a spray (spray with propellent gas or pump-action spray) or an aerosol, in the form of a foam, or in the form of a paste.

Of special importance as cosmetic preparations for the skin are light-protective preparations, such as sun milks, lotions, creams, oils, sunblocks or tropicals, pretanning preparations or after-sun preparations, also skin-tanning preparations, for example self-tanning creams. Of particular interest are sun protection creams, sun protection lotions, sun protection milk and sun protection preparations in the form of a spray.

Of special importance as cosmetic preparations for the hair are the above-mentioned preparations for hair treatment, especially hair-washing preparations in the form of shampoos, hair conditioners, hair-care preparations, e.g. pretreatment preparations, hair tonics, styling creams, styling gels, pomades, hair rinses, treatment packs, intensive hair treatments, hair-straightening preparations, liquid hair-setting preparations, hair foams and hairsprays. Of special interest are hair-washing preparations in the form of shampoos.

A shampoo has, for example, the following composition: from 0.01 to 5% by weight of a UV absorber according to the invention, 12.0% by weight of sodium laureth-2-sulfate, 4.0% by weight of cocamidopropyl betaine, 3.0% by weight of sodium chloride, and water ad 100%.

The cosmetic preparation according to the invention is distinguished by excellent protection of human skin against the damaging effect of sunlight.

EXAMPLES

A. Preparation Examples

Example A-1

Preparation of the Compound of Formula

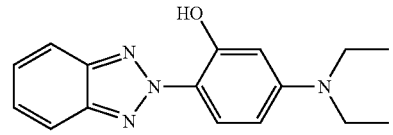

(101)

14.09 g of 2-nitroaniline are suspended in 100 ml water. The suspension is treated with 25 ml of concentrated hydrochloric acid and cooled to 5-10° C. After dropwise addition of a mixture of 6.9 g sodium nitrite in 15 ml water the resulting mixture is stirred for 2 h at 0-5° C. This mixture is then dropped into a solution of 17.7 g 3-diethylaminophenol and 5 ml concentrated hydrochloric acid in 200 ml water at 0-3° C.

The resulting suspension is stirred at 0-1° C. for 1 h. The intermediate is filtered off, washed with water and suspended in 100 ml water. At 60° C. the suspension is treated with 60 ml NaOH (25%) and 19.35 g zinc dust and subsequently stirred at 80° C. for 4 h.

The reaction mixture is cooled down to room temperature and the byproducts are filtered off. The resulting solution is treated with 200 g ice and the pH of the resulting suspension is adjusted to 8 by the addition of concentrated hydrochloric acid.

A beige product precipitates which is isolated by filtration and purified by column chromatography (eluent: toluene/ethyl acetate: 95:5).

UV-spectrum: $\lambda_{max}$ (ethanol)=385 nm, $\epsilon$=29591.

Example A-2

Preparation of the Compound of Formula

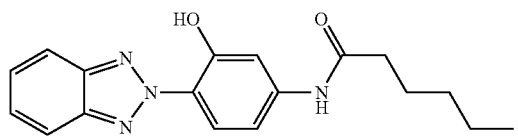

(102)

2.56 g of hexanoyl chloride are added dropwise to a mixture of 3.89 g 5-amino-2-(2H-benzotriazol-2-yl)-phenol (prepared as described for example in the EP 0 751 134 A1) with 10 ml pyridine. The resulting reaction mixture is stirred at 100° C. for 3 h. After cooling down to room temperature the crude product is filtered off and washed 4× with 0.1 molar HCl solution and then 4× with water.

The resulting crystals are recrystallized 2× from isopropanol and 2× from toluene yielding pale beige crystals.

UV-spectrum: $\lambda_{max}$ (ethanol)=346 nm, $\epsilon$=29933.

B. Application Examples

Example B-1

Sun-protection Cream, Type O/W

|  | INCI name | % w/w (as used) |
|---|---|---|
| Part A | Polyglyceryl-3 methylglucose distearate | 2.0 |
|  | Decyl oleate | 5.7 |
|  | Isopropyl palmitate | 5.8 |
|  | Caprylic/capric triglyceride | 6.5 |
|  | UV absorber according to this invention | 2.0 |
|  | Ethylhexyl methoxycinnamate | 5.0 |
|  | Cetyl alcohol | 0.7 |
| Part B | Glycerol | 3.0 |
|  | Carbomer | 0.3 |
|  | Water | q.s. to 100 |
| Part C | Phenoxyethanol (and) methylparaben (and) ethylparaben (and) butylparaben (and) propylparaben (and) isobutylparaben | 0.5 |
| Part D | Methylene bis-benzotriazolyl tetramethylbutylphenol (and) aqua (and) decyl glucoside (and) propylene glycol (and) xanthan gum | 8.0 |
|  | Water | 20.0 |
| Part E | Water (and) sodium hydroxide | q.s. |
|  | Fragrance | q.s. |

Preparation Procedure

Part A and part B are heated separately to 75° C. Part A is poured into part B while stirring. The mixture is homogenised with an Ultra Turrax at 11 000 rpm for 15sec. The mixture is cooled to 60° C. and part C and part D are incorporated. The mixture is homogenised again for a short time (5 sec./11 000 rpm) and further cooled, with moderate stirring. At room temperature, the pH is adjusted with sodium hydroxide solution to between 5.5 and 6.0. Finally, fragrance is added.

The invention claimed is:

1. A method for protecting human and animal hair and skin from harmful effects of UV radiation wherein said method comprises applying to said hair and said skin an effective amount of 2-(2'-Hydroxy-4'-aminophenyl)benzotriazole derivatives of formula

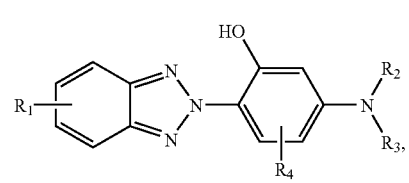

(1)

wherein
$R_1$ and $R_4$ independently of each other are hydrogen; $C_1$-$C_{28}$alkyl; $C_1$-$C_{28}$alkoxy; $C_2$-$C_{28}$alkenyl; $C_2$-$C_{28}$alkinyl; $C_3$-$C_{12}$cycloalkyl; $C_3$-$C_{12}$cycloalkenyl; $C_7$-$C_{28}$aralkyl; $C_1$-$C_{20}$heteroalkyl; $C_3$-$C_{12}$cycloheteroalkyl; or $C_5$-$C_{16}$heteroaralkyl; and wherein $C_1$-$C_{28}$alkyl, $C_1$-$C_{28}$alkoxy, $C_2$-$C_{28}$alkenyl and $C_2$-$C_{28}$alkinyl are unsubstituted or may be substituted by at least one $C_1$-$C_5$alkyl, $C_1$-$C_5$alkoxy or hydroxy;
$R_2$ and $R_3$ independently of each other are hydrogen; $C_1$-$C_{28}$alkyl; $C_2$-$C_{28}$alkenyl; $C_2$-$C_{22}$alkinyl; $C_3$-$C_{12}$cycloalkyl; $C_3$-$C_{12}$cycloalkenyl; $C_7$-$C_{28}$aralkyl; $C_1$-$C_{20}$heteroalkyl; $C_3$-$C_{12}$cycloheteroalkyl; $C_5$-$C_{16}$heteroaralkyl; and wherein $C_1$-$C_{28}$alkyl, $C_1$-$C_{28}$alkoxy, $C_2$-$C_{28}$alkenyl and $C_2$-$C_{28}$alkinyl are unsubstituted or may be substituted by at least one $C_1$-$C_5$alkyl, $C_1$-$C_5$alkoxy or hydroxy; or CO—$R_5$; or
$R_2$ and $R_3$ together with the linking nitrogen form a 5- to 7-membered, monocyclic, carbocyclic or heterocyclic ring;
$R_5$ is $C_1$-$C_{28}$alkyl; $C_2$-$C_{28}$alkenyl; $C_2$-$C_{28}$alkinyl; $C_3$-$C_{12}$cycloalkyl; $C_3$-$C_{12}$cycloalkenyl; $C_7$-$C_{20}$aralkyl; $C_1$-$C_{20}$heteroalkyl; $C_3$-$C_{12}$cycloheteroalkyl; $C_1$-$C_5$alkoxycarbonyl-$C_1$-$C_5$alkyl; or $C_5$-$C_{16}$heteroaralkyl; and
n is 1, 2, 3 or 4.

2. The method according to claim 1, wherein formula (1) $R_1$ is hydrogen; $C_1$-$C_{28}$alkyl; or $C_1$-$C_{28}$alkoxy.

3. The method according to claim 2, wherein formula (1) $R_1$ is hydrogen; $C_1$-$C_5$alkyl; or $C_1$-$C_5$alkoxy.

4. The method according to claim 3, wherein formula (1) $R_1$ is hydrogen; methyl, tert. butyl; or methoxy.

5. The method according to claim 1, wherein $R_4$ is hydrogen.

6. The method according to claim 1, wherein $R_2$ is hydrogen; $C_{1-C28}$alkyl; $C_2$-$C_{28}$alkenyl; and wherein $C_1$-$C_{28}$alkyl and $C_2$-$C_{28}$alkenyl are unsubstituted or may be substituted by at least one $C_1$-$C_5$alkyl, $C_1$-$C_5$alkoxy or hydroxy; or CO—$R_5$; and
$R_5$ is $C_1$-$C_{28}$alkyl; $C_1$-$C_5$alkoxycarbonyl-$C_1$-$C_5$alkyl; or $C_3$-$C_{12}$cycloalkyl.

7. The method according to claim 6, wherein formula (1)
  $R_2$ is hydrogen; $C_1$-$C_{10}$alkyl; $C_2$-$C_{10}$alkenyl; and wherein $C_2$-$C_{10}$alkenyl is unsubstituted or may be substituted by $C_1$-$C_5$alkoxy; or CO—$R_5$; and
  $R_5$ is $C_1$-$C_{10}$alkyl; $C_1$-$C_5$alkoxycarbonyl-$C_1$-$C_5$alkyl; or $C_3$-$C_{12}$cycloalkyl.

8. The method according to claim 7, wherein formula (1)
  $R_2$ is hydrogen; $C_1$-$C_5$alkyl; *-$C_1$-$C_4$alkylene-HC=CH—O—$C_1$-$C_5$alkyl; or CO—$R_5$;
  $R_5$ is $C_1$-$C_{10}$alkyl; —$CH_2$-$CH_2$(CO)—O—$C_2H_5$; or cyclohexyl.

9. The method according to claim 8, wherein formula (1) $R_5$ is isooctyl.

10. The method according to claim 1, wherein formula (1) $R_3$ is hydrogen; or *-(CO)—$CH_3$.

11. The method according to claim 1, wherein $R_2$ and $R_3$ have the same meaning.

12. The method according to claim 11, wherein $R_2$ and $R_3$ are $C_1$-$C_5$alkyl.

13. The method according to claim 1, wherein formula (1) $R_2$ and $R_3$ together with the linking nitrogen form the heterocyclic ring radical of formula.

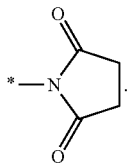

(1a)

14. The method according to claim 1, wherein formula (1)
  $R_1$ is hydrogen; $C_1$-$C_5$alkyl; or $C_1$-$C_5$alkoxy;
  $R_4$ is hydrogen; or $C_1$-$C_5$alkyl;
  $R_2$ is hydrogen; $C_1$-$C_{10}$alkyl; $C_2$-$C_{10}$alkenyl; and wherein $C_2$-$C_{10}$alkenyl is unsubstituted or may be substituted by $C_1$-$C_5$alkoxy; or CO—$R_5$;
  $R_5$ is $C_1$-$C_{10}$alkyl; $C_1$-$C_5$alkoxycarbonyl-$C_1$-$C_5$alkyl; or $C_3$-$C_{12}$cycloalkyl; and
  $R_3$ is hydrogen; or *-(CO)—$CH_3$.

15. The method according to claim 14, wherein
  $R_1$ is hydrogen; or $C_1C_5$alkyl;
  $R_2$ is CO—$R_5$;
  $R_3$ is hydrogen;
  $R_5$ is isooctyl; and
  $R_4$ is hydrogen.

16. A cosmetic preparation comprising at least one compound of formula (1) together with cosmetically tolerable carriers or adjuvants

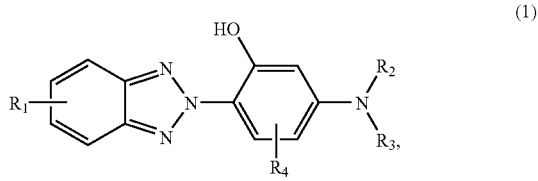

(1)

wherein
  $R_1$ and $R_4$ independently of each other are hydrogen; $C_1$-$C_{28}$alkyl; $C_1$-$C_{28}$alkoxy; $C_2$-$C_{28}$alkenyl; $C_2$-$C_{28}$alkinyl; $C_3$-$C_{12}$cycloalkyl; $C_3$-$C_{12}$cycloalkenyl; $C_7$-$C_{28}$ aralkyl; $C_1$-$C_{20}$heteroalkyl; $C_3$-$C_{12}$cycloheteroalkyl; or $C_5$-$C_{16}$ heteroaralkyl; and wherein $C_1$-$C_{28}$alkyl, $C_1$-$C_{28}$alkoxy, $C_2$-$C_{28}$alkenyl and $C_2$-$C_{28}$alkinyl are unsubstituted or may be substituted by at least one $C_1$-$C_5$alkyl, $C_1$-$C_5$alkoxy or hydroxy;
  $R_2$ and $R_3$ independently of each other are hydrogen; $C_1$-$C_{28}$alkyl; $C_2$-$C_{28}$ alkenyl; $C_2$-$C_{22}$alkinyl; $C_3$-$C_{12}$cycloalkyl; $C_3$-$C_{12}$cycloalkenyl; $C_7$-$C_{28}$aralkyl; $C_1$-$C_{20}$heteroalkyl; $C_3$-$C_{12}$cycloheteroalkyl; $C_5$-$C_{16}$heteroaralkyl; and wherein $C_1$-$C_{28}$alkyl, $C_1$-$C_{28}$alkoxy, $C_2$-$C_{28}$alkenyl and $C_2$-$C_{28}$alkinyl are unsubstituted or may be substituted by at least one $C_1$-$C_5$alkyl, $C_1$-$C_5$alkoxy or hydroxy; or CO—$R_5$; or
  $R_2$ and $R_3$ together with the linking nitrogen form a 5- to 7-membered, monocyclic, carbocyclic or heterocyclic ring;
  $R_5$ is $C_1$-$C_{28}$alkyl; $C_2$-$C_{28}$alkenyl; $C_2$-$C_{28}$alkinyl; $C_3$-$C_{12}$cycloalkyl; $C_3$-$C_{12}$cycloalkenyl; $C_7$-$C_{20}$aralkyl; $C_1$-$C_{20}$heteroalkyl; $C_3$-$C_{12}$cycloheteroalkyl; $C_1$-$C_5$alkoxycarbonyl-$C_1$-$C_5$alkyl; or $C_5$-$C_{16}$heteroaralkyl; and
  n is 1, 2, 3 or 4.

17. A cosmetic preparation according to claim 16 wherein said preparation is an anti-wrinkle perception modifier.

* * * * *